US007404670B2

(12) United States Patent
Willis

(10) Patent No.: US 7,404,670 B2
(45) Date of Patent: Jul. 29, 2008

(54) ANALYTICAL FURNACE WITH PREDICTIVE TEMPERATURE CONTROL

(75) Inventor: Peter M. Willis, Benton Harbor, MI (US)

(73) Assignee: Leco Corporation, St. Joseph, MI (US)

(*) Notice: Subject to any disclaimer, the term of this patent is extended or adjusted under 35 U.S.C. 154(b) by 742 days.

(21) Appl. No.: 10/791,456

(22) Filed: Mar. 2, 2004

(65) Prior Publication Data
US 2004/0173142 A1    Sep. 9, 2004

Related U.S. Application Data

(60) Provisional application No. 60/452,594, filed on Mar. 6, 2003.

(51) Int. Cl.
*H05B 1/02* (2006.01)
(52) U.S. Cl. .................. 374/14; 219/497; 219/483; 392/418
(58) Field of Classification Search .............. 219/497, 219/505, 506, 483–486; 392/416–418; 118/723 R; 438/660
See application file for complete search history.

(56) References Cited

U.S. PATENT DOCUMENTS

| 4,009,605 A | 3/1977 | Kober |
| 4,197,273 A | 4/1980 | Dusserre et al. |
| 4,248,315 A | 2/1981 | Falinower |
| 4,303,615 A | 12/1981 | Jarmell et al. |
| 4,404,461 A | 9/1983 | Sitek et al. |
| 4,522,788 A | 6/1985 | Sitek et al. |
| 4,565,598 A * | 1/1986 | Seymour .................. 117/15 |
| 4,944,925 A | 7/1990 | Yamauchi et al. |
| 5,449,883 A * | 9/1995 | Tsuruta .................. 219/483 |
| 5,517,594 A * | 5/1996 | Shah et al. .............. 392/416 |
| 6,110,274 A | 8/2000 | Okuno |

(Continued)

FOREIGN PATENT DOCUMENTS

GB    653513    5/1951

(Continued)

OTHER PUBLICATIONS

American National Standard ANSI/ASTM D 3172-73 (Reapproved 1979), Standard Method for Proximate Analysis Of Coal and Coke, pp. 386-395.

(Continued)

*Primary Examiner*—Mark Paschall
(74) *Attorney, Agent, or Firm*—Price, Heneveld, Cooper, DeWitt & Litton, LLP

(57) ABSTRACT

An analytical furnace includes a predictive temperature control which is trained to model crucible temperature during analysis by employing a pair of temperature sensors, with one sensor being mounted in the furnace in fixed relationship and a second sensor which can be positioned within a crucible for training and tuning a crucible temperature profile, such that the crucible temperature in which a sample is placed is modeled and its response to the application of energy to the furnace in accordance with the furnace's dynamic thermal characteristics is known. By modeling the temperature profile within a crucible, the furnace can be controlled to provide a faster, more accurate analysis and prevent excessive overshooting of temperature as desired temperature plateaus are approached.

15 Claims, 8 Drawing Sheets

U.S. PATENT DOCUMENTS 6,730,885 B2 * 5/2004 Suzuki et al. ............... 219/486
2005/0266685 A1 * 12/2005 Nakano et al. .............. 438/660

FOREIGN PATENT DOCUMENTS

GB 702578 1/1954

OTHER PUBLICATIONS

CEM Corporation, "Moisture/Solids Analyzer AVC-80" literature, 1981.
Fisher Scientific Company, "Fisher Sulfur Analyzer System" literature, Apr. 1981.

* cited by examiner

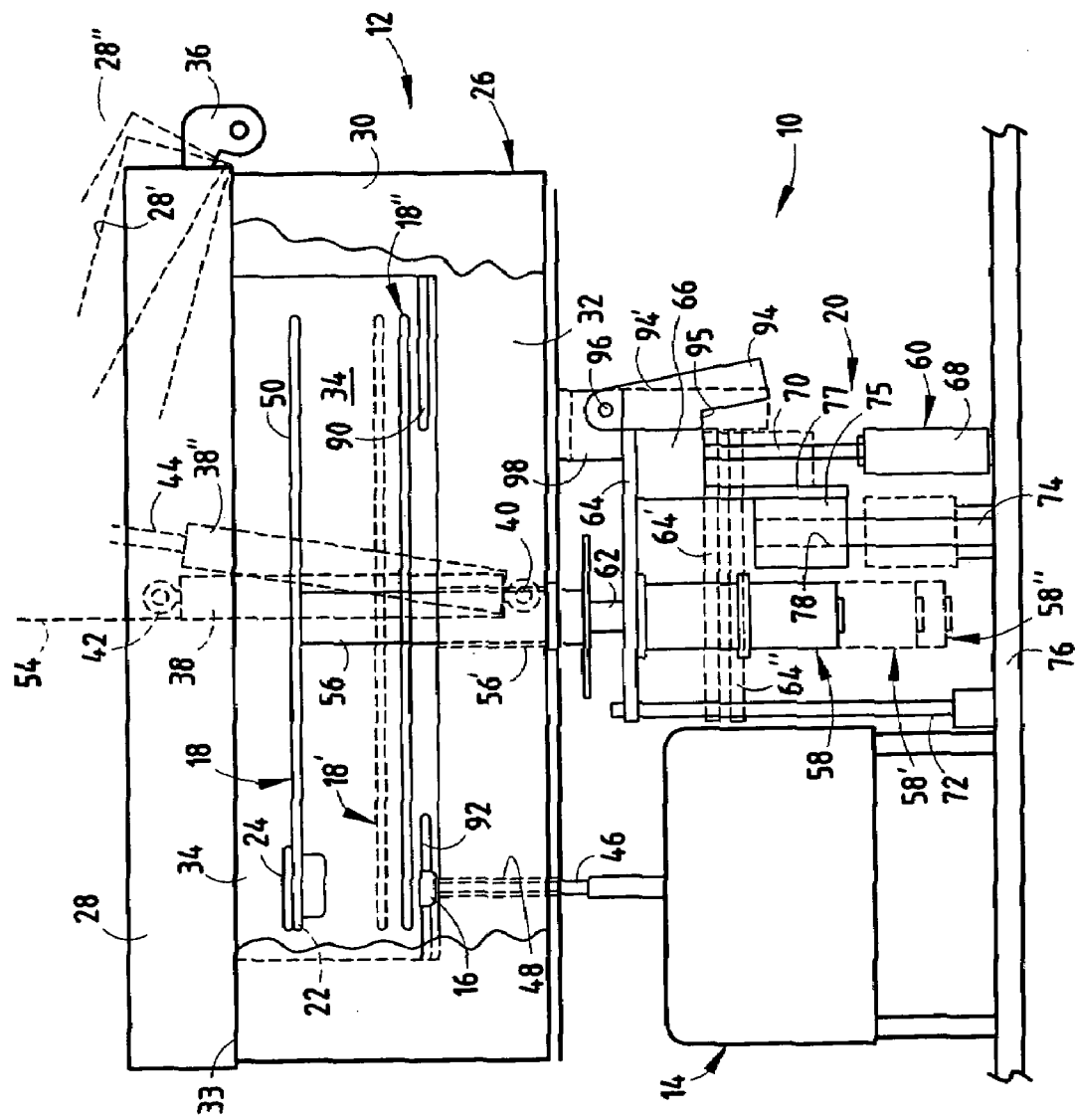

ANALYTICAL FURNACE WITH PREDICTIVE TEMPERATURE CONTROL

CROSS-REFERENCE TO RELATED APPLICATIONS

This application claims priority under 35 U.S.C. § 119(e) on U.S. Provisional Application No. 60/452,594 entitled ANALYTICAL FURNACE WITH PREDICTIVE TEMPERATURE CONTROL, filed on Mar. 6, 2003, by Peter M. Willis, the entire disclosure of which is incorporated herein by reference.

BACKGROUND OF THE INVENTION

The present invention relates to an analytical furnace and particularly to an analytical furnace having a predictive temperature control.

Many laboratory analyzers employ combustion or other types of furnaces which heat and/or combust a sample for the determination of chemical elements in the sample. One type of analyzer is a thermogravametric analyzer which employs a furnace, the temperature of which must be carefully controlled. The thermogravametric analyses of materials provide important information as to moisture content, volatiles, ash, or fixed carbon, as well as weight loss or gain on ignition. Materials, such as coal, coke, graphite, flour, dough, plant tissue, feeds, fertilizer, food stuffs, chemicals, rubbers, plastics, ceramics, minerals, soils, sediments, and paper, are all capable of thermogravametric analysis utilizing ASTM standards, which detail the requirements for determining the moisture, volatiles, fixed carbon, ash content, and ignition content of materials. The determinations are made by first weighing a sample to be analyzed and then subjecting the sample to a well controlled time/temperature profile in a controlled atmosphere and weighing the sample during the control period to determine weight loss at different temperatures. Well known mathematical formulas are then employed to calculate the moisture, volatiles, fixed carbon, ash, and ignition content of the material. It is of primary importance that the temperature profile is accurately known and precisely controlled, particularly where sample material can loose discrete percentages of its weight at distinct temperatures.

Prior art analyzers performing sample analyses and analyzers performing multiple sample thermogravametric analyses typically use a furnace having a single temperature sensor, which, although providing adequate analysis information, can suffer from slow operation and less than desirable accuracy in performance. Thus, there is a need for an analytical furnace, such as for use with a thermogravametric analyzer in which the temperature within a sample-holding crucible is accurately determined and can be precisely controlled. There further exists a need for an analytical furnace which improves the speed of analyses and which has repeatability from analysis to analysis and reproducibility from instrument to instrument so that accurate, fast analyses can be obtained.

SUMMARY OF THE INVENTION

The system of the present invention provides an analytical furnace with a predictive temperature control. In one embodiment, a batch-type macro thermogravametric analyzer is provided which is capable of analyzing multiple samples rapidly and accurately by providing a predictive temperature control utilizing at least a pair of temperature sensors in the furnace. One sensor is mounted in fixed relationship in the furnace, and a second sensor is mounted within a crucible for training and tuning the temperature profile, such that the crucible temperature in which a sample is placed can be modeled and its response to the application of energy to the furnace in accordance with the furnace's dynamic thermal characteristics known, predictable and controllable. By employing a pair of temperature sensors, with one being located in a crucible during the modeling of the temperature profile within the crucible, the furnace can be controlled to provide a faster, more accurate analysis and prevent excessive overshooting of temperature as desired temperature plateaus are more quickly approached.

The thermogravametric analyzer of the present invention includes a furnace, a balance with a weigh platform positioned within the furnace, a support for a plurality of crucibles which sequentially positions a crucible on the weigh platform, a heater for heating the furnace, and a pair of temperature sensors. A first temperature sensor is positioned in fixed relationship within the furnace, and a second temperature sensor is movable to be positioned within a crucible on the support. A control circuit is coupled to the sensors and includes a microprocessor programmed to obtain temperature data during training and tuning modes which model the crucible temperature as the furnace temperature is increased and to control the furnace temperature during an operational mode. The resultant furnace temperature control is precise and provides faster, more accurate, and repeatable analyses of samples.

These and other features, objects and advantages of the present invention will become apparent upon reading the following description thereof together with reference to the accompanying drawings.

BRIEF DESCRIPTION OF THE DRAWINGS

FIG. 4 is a side elevational view, partly broken away and partly in phantom form, of the thermogravametric analyzer embodying the present invention;

DETAILED DESCRIPTION OF THE PREFERRED EMBODIMENT

Figure 1:
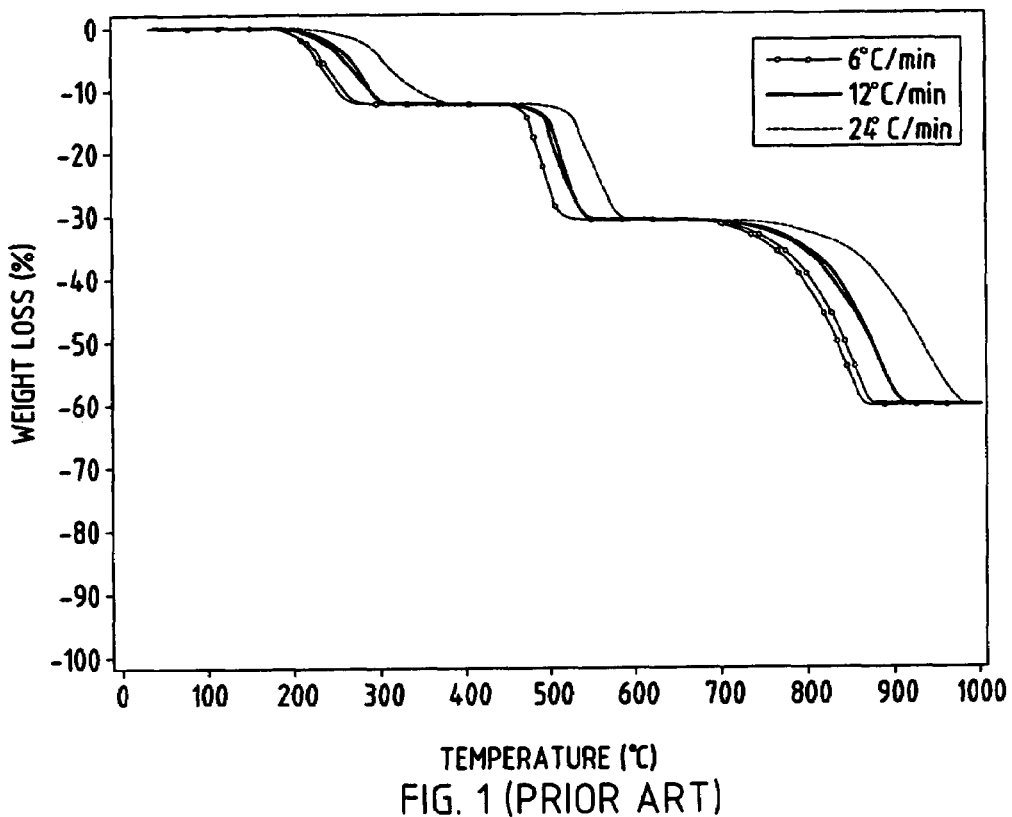
FIG. 1 is a weight loss verses temperature graph for a prior art thermogravametric analyzer.

Referring initially to FIG. 1, there is shown a typical analysis cycle for samples, such as 10 gram samples, in a macro batch thermogravametric analyzer of the prior art, such as disclosed in U.S. Pat. No. 4,522,788. The graph illustrates the percent of weight loss at different temperature levels as the furnace temperature is increased from ambient to a maximum of approximately 1000° C. during an analysis of a sample. As can be seen with the different temperature ramp rates (i.e., 6° C. per minute verses 24° C. per minute), the reported weight loss verses temperature profile of a sample within a crucible varies significantly.

Figure 2:
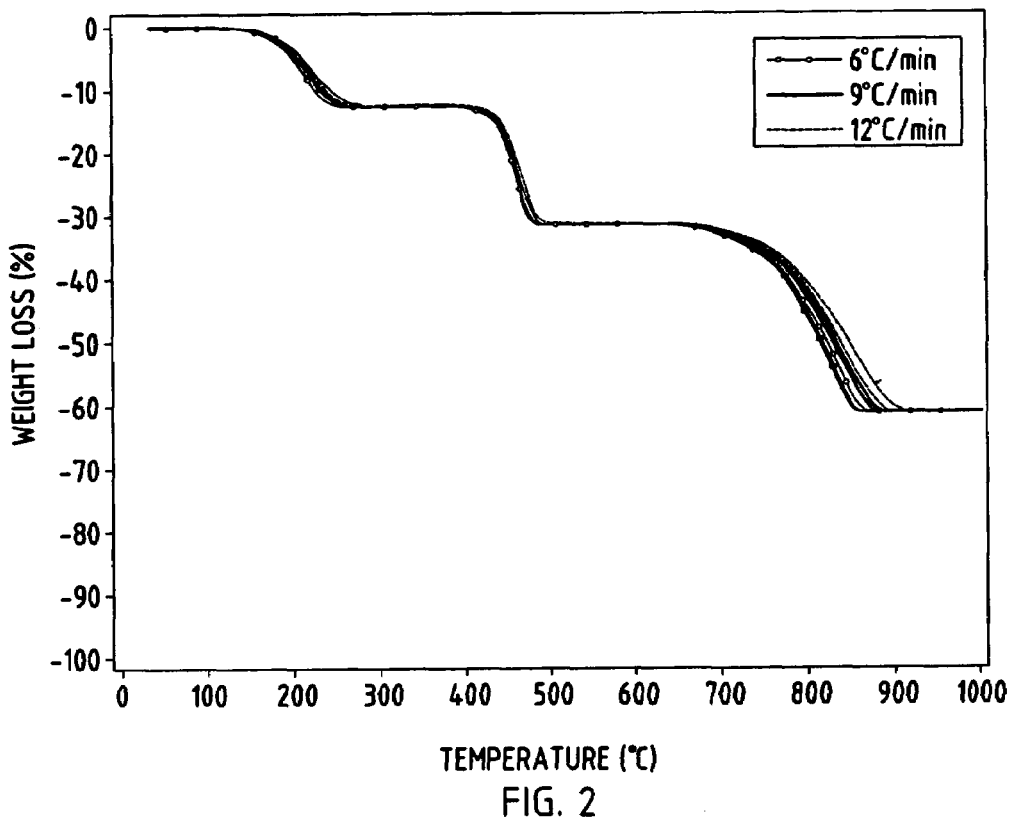
FIG. 2 is a weight loss verses temperature graph of the performance of the system of the present invention.
Figure 3:
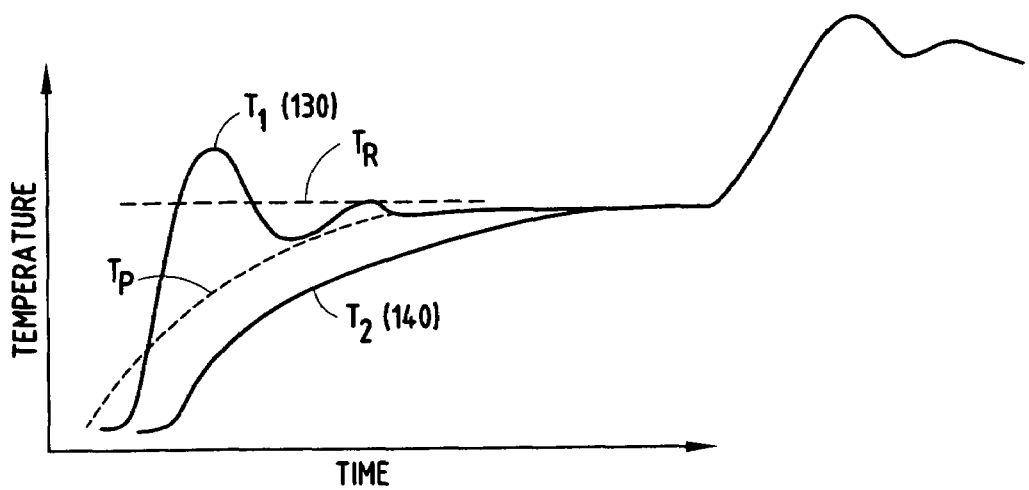
FIG. 3 is a graph of temperature verses time in the thermogravametric furnace of the present invention, showing the measured and predicted temperatures within the furnace during an initial phase of an analysis.

The graph of FIG. 2 illustrates the improved performance achieved by the thermogravametric analyzer of the present invention using a predictive temperature control employing two sensors, one fixedly located within the furnace and one located within a crucible during a crucible modeling mode. As seen in FIG. 2, the percent weight loss verses temperature results in relatively tight overlying curves for furnace temperature ramp rates between 6° C. and 12° C. per minute, resulting in an analysis of a sample that is independent of temperature ramp rate. The predictive control of temperature is illustrated in the graph of FIG. 3, in which curve $T_1$ corresponds to the temperature detected in the furnace by a first temperature sensor 130 (shown in FIGS. 5, 6, and 8), a temperature curve $T_2$ of a second temperature sensor 140 positioned in a crucible (also shown in FIGS. 5, 6, and 8), and a predicted modeled crucible temperature, shown by the dotted line curve $T_P$ which is developed utilizing software described below in connection with the flow diagrams of FIGS. 9-11. By modeling the crucible temperature response and predicting what the crucible temperature will be as different temperature plateaus are reached, overshoot of temperature is substantially avoided and the estimated thermal delay of temperature $T_2$ in the actual crucible can be removed from the feedback path to enable a more responsive control. Having briefly described the improved results which can be achieved by the thermogravametric analyzer of the present invention, a description of the analyzer, its control circuit, and the programming of the computer to achieve these results is now presented beginning with FIGS. 4-6.

A thermogravametric analyzer in accordance with a preferred embodiment of the invention is illustrated in FIG. 4 and generally designated 10. As seen in FIG. 4, analyzer 10 includes a furnace 12, an electronic balance 14 having weigh platform 16 positioned within the furnace, a sample platter 18 positioned within the furnace, and a platter operation mechanism 20 supporting platter 18 within the furnace. Sample rack 18 is a disc having a plurality of apertures 22 positioned evenly about the periphery of the platter (see also FIGS. 5 and 6). A plurality of sample-containing crucibles 24 may be positioned on platter 18 with one of the crucibles generally aligned with each one of apertures 22 and supported by the peripheral edge of the aperture. Mechanism 20 is then actuated to sequentially and individually deposit crucibles 24 on weigh platform 16 by rotating platter 18 so that one of apertures 22 is aligned with weigh platform 16 and then lowering platter 18 to deposit the associated crucible on the weigh platform. After weighing is complete, platter 18 is shifted upwardly to lift the weighed crucible off of weigh platform 16, and the next adjacent crucible is weighed in a similar manner. As a result, crucibles 24 are sequentially weighed within furnace 12 without opening the furnace.

Figure 7:
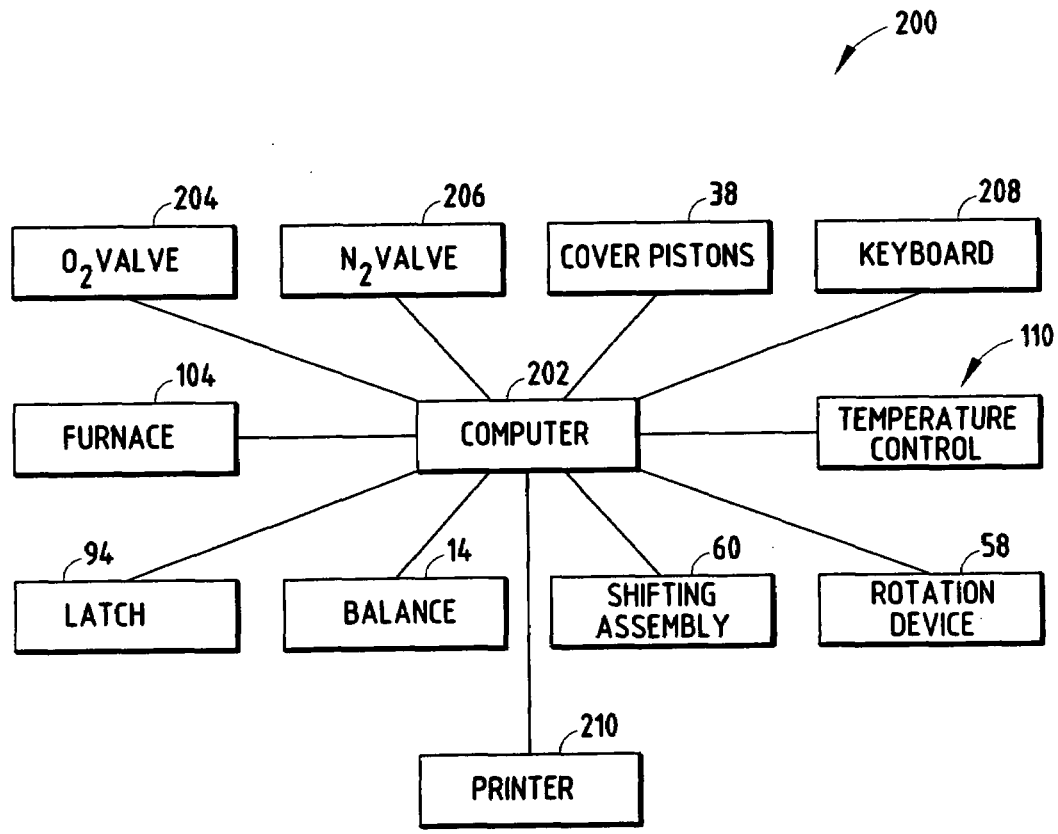
FIG. 7 is a block electrical circuit diagram of the control circuit for the thermogravametric analyzer.

Referring more specifically to the construction of furnace 12, it is seen that the furnace includes lower containing member 26 and a cover 28, which together define a chamber 34 having a volume of approximately three liters. Lower member 26 includes a generally cylindrical side wall 30 integrally joined to generally horizontal, planar furnace floor 32. The upper end of member 26 is open with wall 30 terminating with an annular top surface 33. Cover 28 is a generally planar member having a circular shape and, when closed, rests on the upper surface 33 of wall 30. Resistive heating elements 104 (FIGS. 6 and 7) are positioned within furnace 12 and are controlled with the temperature control circuit 110 (FIG. 7), which operates as described below to regulate the temperature of the furnace at desired temperatures between about 50° C. and about 1000° C. Both lower member 26 and cover 28 are fabricated from well-known refractory ceramic materials, such as alumina.

Cover 28 is hingedly secured to member 26 by a hinge 36 for movement between a closed position resting on surface 33 of lower member 26, as indicated in FIG. 4; a load position indicated in phantom at 28'; and an open position indicated in phantom as 28". A pair of conventional pneumatic cylinders 38 are mounted on opposite sides of furnace 12 and are pivotally mounted to and between member 26 and cover 28 at pivot points 40 and 42, respectively. Each cylinder 38 includes a rod 44 which is telescopically received within the cylinder body and telescopes outwardly therefrom when pneumatic pressure is applied to the cylinder to move cover 28 between the closed, load 28', and open 28" positions. When cover 28 is in its fully open position 28", cylinders 38 are positioned as indicated in FIG. 1 at 38".

The electronic balance 14 includes a weigh platform 16 supported on shaft 46. Shaft 46 extends vertically and is located within a generally cylindrical bore 48 formed in furnace floor 32. The inside diameter of bore 48 is somewhat larger than the outer diameter of shaft 46 so that the shaft is freely movable within the bore.

Sample platter 18 (FIGS. 4-6) comprises a generally planar disc-shaped plate 50 capable of withstanding temperatures of at least 1000° C. Plate 50 includes twenty evenly spaced circular apertures 22 extending therethrough near the outer periphery of the platter. One aperture is designated the zero-position aperture, and each of apertures 22 has generally the same diameter. The circular configuration of apertures 22 and plate 50 have a common vertical axis 54 (FIG. 4) about which sample platter 18 rotates. Since the center of each aperture is the same distance from axis 54, by rotating platter 18, any one of apertures 22 may be vertically aligned with weigh platform 16.

Elevation and rotation structure 20 are provided to selectively raise platter 18, rotate the platter, and subsequently lower the platter to sequentially place a sample-holding crucible 24 on weigh platform 16. Structure 20 (FIG. 4) includes a shaft 56 supporting platter 18 and a lower shaft 62 extending from a motor 58 which is mounted to plate 64 and which may be actuated to rotate platter 18 to position any one of apertures 22 in vertical and horizontal alignment with weigh platform 16. Shaft 56 extends vertically through bore 56' in the floor 32 of member 26 and has an upper end secured to the center of support plate 50.

Structure 20 further includes a lift 60 which includes horizontal support plate 64, rod block 66 fixedly secured to the underside of plate 64, and a pneumatic cylinder 68 having shaft 70 fixedly secured to block 66. Consequently, when pneumatic pressure is applied to cylinder 68, shaft 70 extends from the cylinder upwardly shifting rod block 66 and support plate 64 to which the platter-rotating means, including motor 58, is mounted. When the pneumatic pressure is released from cylinder 68, shaft 70, block 66, and support plate 64 move downwardly. Guide block 75 is fixedly secured to leg 77 of rod block 66 and includes an aperture 78 for receiving guide 74 extending upwardly from base 76 of analyzer 10. A second guide rod 72 extends slidably through an aperture in plate 64 such that the plate 64 and platter 18 rotatably coupled thereto are held in precise rotational alignment when the platter is raised and lowered by the actuation of cylinder 68.

By controlling pneumatic cylinder 68, support plate 64 may be vertically shifted between a raised load position shown in solid lines in FIG. 4, a somewhat lowered rotate position 64', and a lowermost weigh position 64". Because rotation device or motor 58 travels vertically with plate 64, it also moves vertically between a load position shown in FIG. 4, a rotate position 58', and a weigh position 58'. Finally, because shaft 56 moves vertically with rotation device 58, platter 18 is vertically shiftable between a load position shown in FIG. 4, a rotate position 18', and a weigh position 18". In the load position, rack 18 is proximate the upper open end of furnace 12 to facilitate the positioning of crucibles 24 in apertures 22.

A latch 94 is pivotally mounted at 96 to a support bracket 98 and is pivotable between an unlocked position shown in FIG. 4 and a locked position 94' shown in phantom form. Latch 94 includes a locking edge 95 which does not interfere with the movement of plate 64 when latch 94 is in its unlocked position. However, when platter 18 is in either rotate or weigh positions 18' or 18", respectively, latch 94 may be pivoted downwardly to its locked position wherein edge 100 is located directly above plate 64. Platter 18 may then not be raised to load position 18' until latch 94 is unlocked. The mechanical operation of the analyzer 10 is described in greater detail in U.S. Pat. No. 4,522,788, the disclosure of which is incorporated herein by reference.

Figure 5:
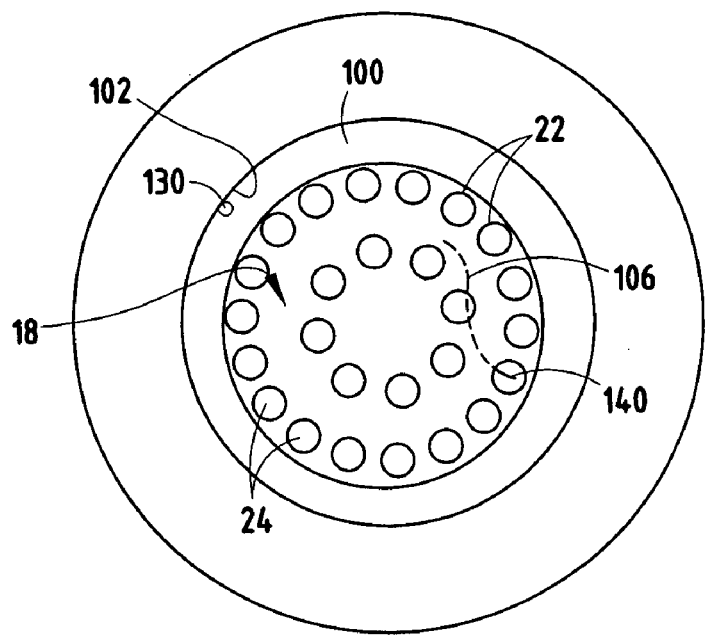
FIG. 5 is a top plan view of the furnace chamber of FIG. 4.
Figure 6:
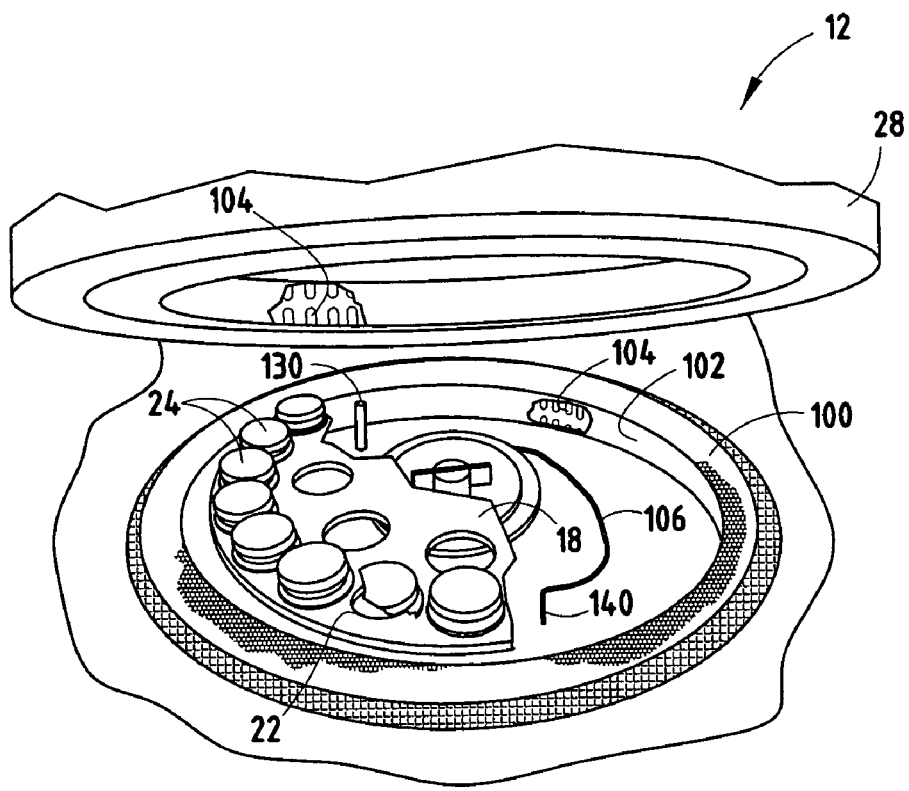
FIG. 6 is a perspective view, partly broken away, of the furnace chamber of FIG. 4.
Figure 8:
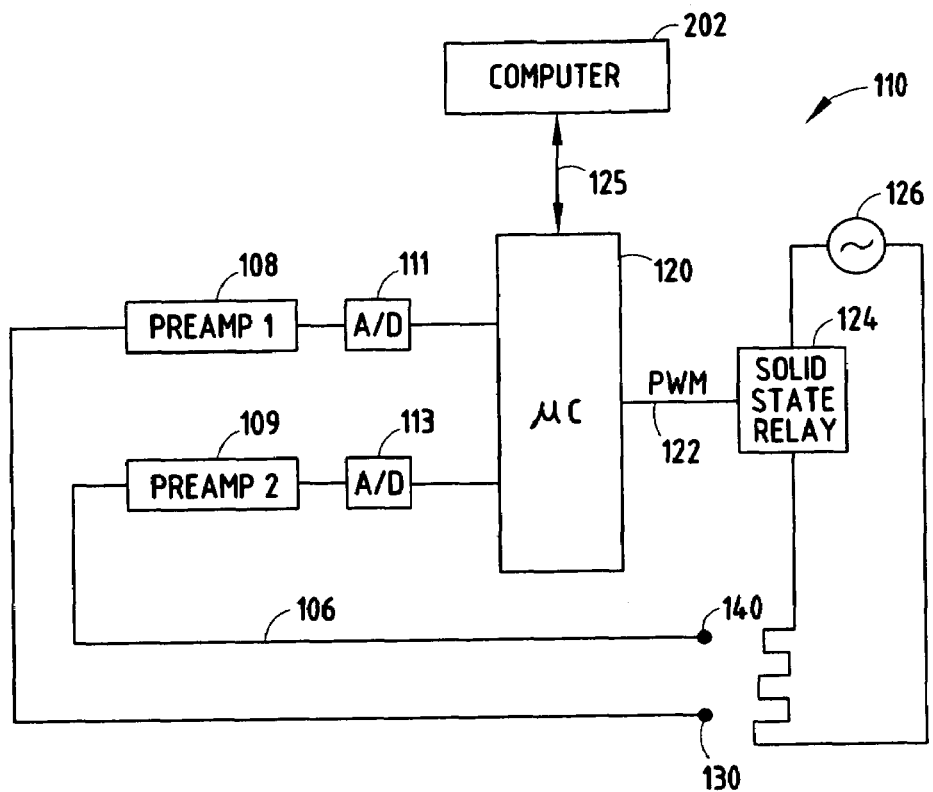
FIG. 8 is a detailed block diagram of the temperature control shown in FIG. 7.

Turning now to FIGS. 5 and 6, there is shown a plan perspective view of the furnace in which a temperature sensor 130 is positioned in the furnace chamber 100 surrounding the platter 18 and in fixed relationship to the furnace wall 102, which is made, as noted above, of a suitable ceramic material in which there is embedded a resistance heater 104 (FIGS. 6 and 8). Temperature sensor 130 provides a signal to the control circuit representing the temperature of the furnace at this fixed location within the furnace chamber 100. A second temperature sensor 140, such as a thermocouple, is coupled by a flexible conductor 106 extending through the furnace wall in a conventional manner and is insertable within a crucible 24 approximately 90° from the fixed temperature sensor 130 to provide actual crucible temperature information for training of the control circuit to allow the improved predictive temperature control illustrated in FIGS. 2 and 3. Conductor 106 is approximately 20 inches long, in one embodiment, to position thermocouple 140 in a position spaced from 130 and is representative of the crucible temperature during an analysis. Thus, by measuring the actual temperature in a crucible and comparing it to the furnace temperature sensed by sensor 130, the additional temperature information is used, as described in greater detail below, to provide the improved analytical results.

Temperature sensors 130 and 140 can be thermocouples or other suitable temperature sensors capable of withstanding the furnace temperature which reaches a maximum of approximately 1000° C. The temperature sensors are coupled to a temperature control circuit 110 (FIG. 8) which, in turn, is part of the overall control system 200, shown in FIG. 7. Control 200 includes a microprocessor 202 coupled by suitable interface circuits to the furnace heater 104, an oxygen valve 204, a controlled nitrogen valve 206, the cover actuating pistons 38, an input keyboard 208, the latch mechanism including cylinder 94, electronic balance 14, the platter shifting assembly 60, and the rotation device 58. The temperature control circuit 110 provides signal input information from thermocouples 130 and 140 through preamplifiers 108, 109, as seen in FIG. 8, through A-to-D converters 111, 113, respectively, to inputs of a microprocessor 120, which is coupled by a data bus 125 to computer 202. Microprocessor 120 may be an Intel 8051. Computer 202 responds to the temperature information provided by microprocessor 120 to provide training and tuning and the resultant modeling of the crucible temperature response within the furnace as described in connection with the program flow diagrams discussed below. The resultant control signals from computer 202 to microprocessor 120 provides pulse width modulated signals at output 122 (FIG. 8) to a solid state relay 124 coupled to a source of operating power 126 for supplying operating power through relay 124 to heating element 104 of the furnace 12. Computer 202 is also coupled to a printer 210 for providing the operator with a printout of the analytical results which may, for example, include a graph, such as shown in FIG. 2, and specific data for each sample being analyzed.

The concept behind the training and tuning of the furnace control 200 is to derive a model for the furnace temperature dynamics which is representative of the actual crucible temperature which cannot be measured during the dynamic motion of the platter 18 with crucibles thereon during an analysis of several samples but can be predicted by the temperature sensed by the fixed sensor 130 based upon prior training and tuning and the resultant stored modeling data of the crucible temperature. Because crucible temperature sensor 140 is located further from the heating elements 104 than sensor 130, the measurement at 140 includes a transport delay that often makes precise control more difficult. The crucible model is therefore divided into two sections: first being the modeled dynamics; and secondly the transport delay. Both the modeled dynamics and transport delay are temperature dependent and, therefore, must be determined at various temperatures between ambient and the maximum furnace operating temperature of 1000° C. Model and delay parameters may then be continuously interpolated at all temperatures between ambient and 1000° C.

During the training mode, the temperature is stepwise increased in 100° C. increments in ten steps between ambient and 1000° C., with the first increment TR at 100° C. as shown in FIG. 3, showing the temperature response of the thermocouples 130 and 140. This information is recorded for each temperature step by both thermocouples 130 and 140. Knowing the temperature $T_1$ and the recorded and processed data for a given furnace, the desired temperature target can be more quickly and accurately reached. The software utilizes a proportional, integral, and derivative (PID) algorithm for providing temperature control signals for the furnace control circuit 110 (shown in FIG. 8) as described in connection with the algorithm flow diagrams described below.

Figure 9A:
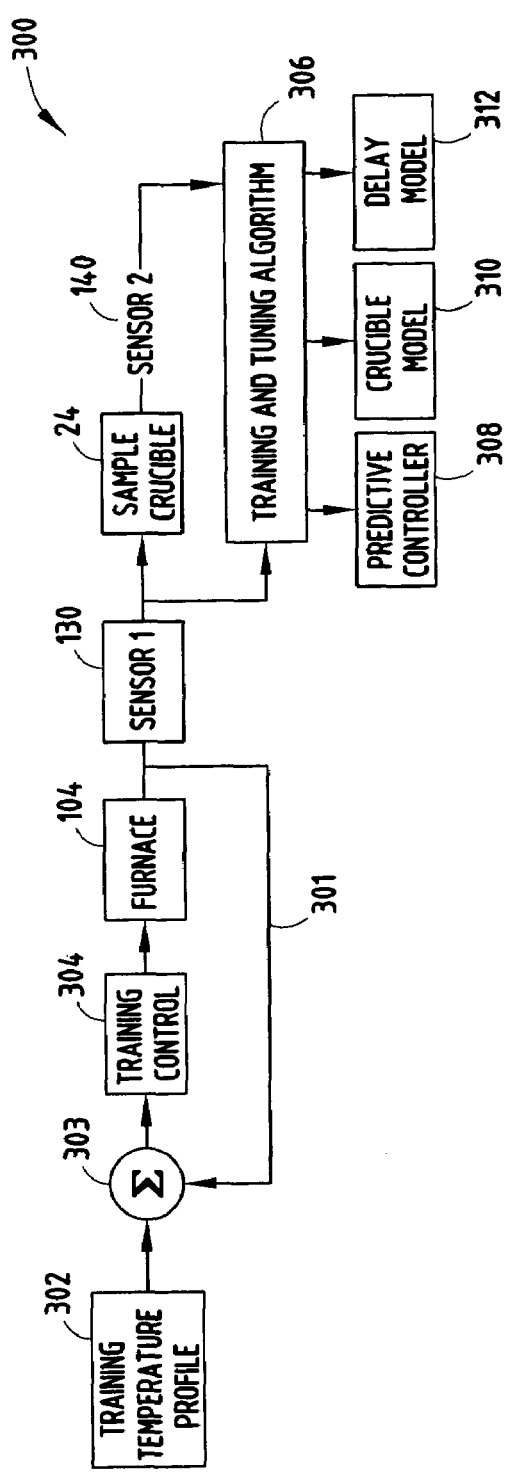
FIGS. 9A and 9B are flow diagrams showing an overview of the predictive temperature furnace control for the analyzer of the present invention.
Figure 9B:
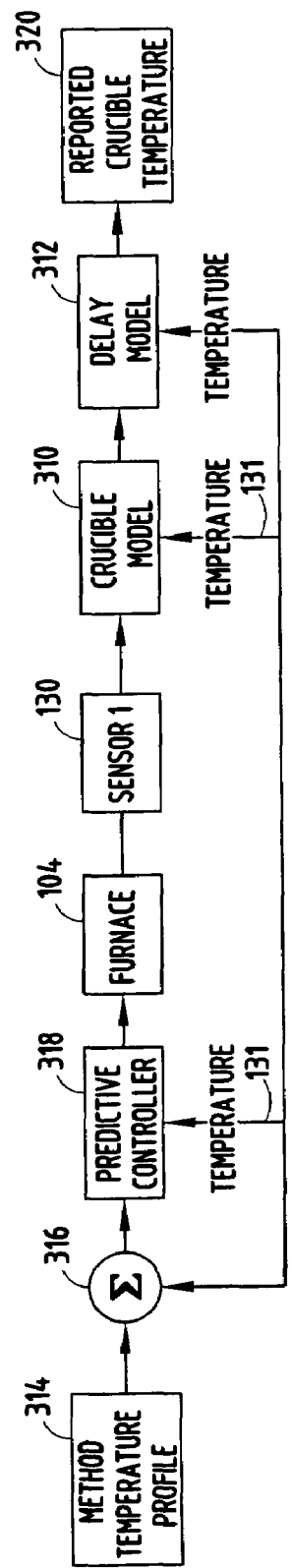

In FIGS. 9A and 9B, the basic training, tuning, and operational modes are described in flow diagram 300 (FIG. 9A). The training mode is described in detail in connection with FIG. 10, and the tuning mode is described in detail in connection with FIGS. 11a and 11b. The operational mode, which follows the training and tuning modes, is shown in FIG. 9B.

Referring now to FIG. 9A, the training and tuning mode operation 300 is broadly set forth and, as indicated by block 302, the training temperature profile is entered, including incremental steps of 100° C. for the furnace temperature. The algorithm proceeds through a summation node 303 to actuate the training controller 304, which provides control signals to the furnace 104. Temperature sensor 130 provides a temperature feedback signal, as indicated by line 301 to the input of the training controller 304 to control the response to a first temperature plateau. Additionally, the temperature in a sample crucible 24 is detected by temperature sensor 140 and the input from both temperature sensors 130 and 140 are applied to the training and tuning algorithm of FIGS. 10 and 11, as indicated by block 306 and described in greater detail below. The training and tuning algorithm 306 results in a predictive controller, as shown by block 308, determined by the tuning algorithm of FIGS. 11A and 11B, and a crucible temperature model 310, as determined by the training program of FIG. 10 and a temperature delay model 312 also as determined by the training program of FIG. 10. The training mode algorithm is now described in connection with FIG. 10, followed by a description of the tuning algorithm of FIGS. 11A and 11B.

Figure 10:
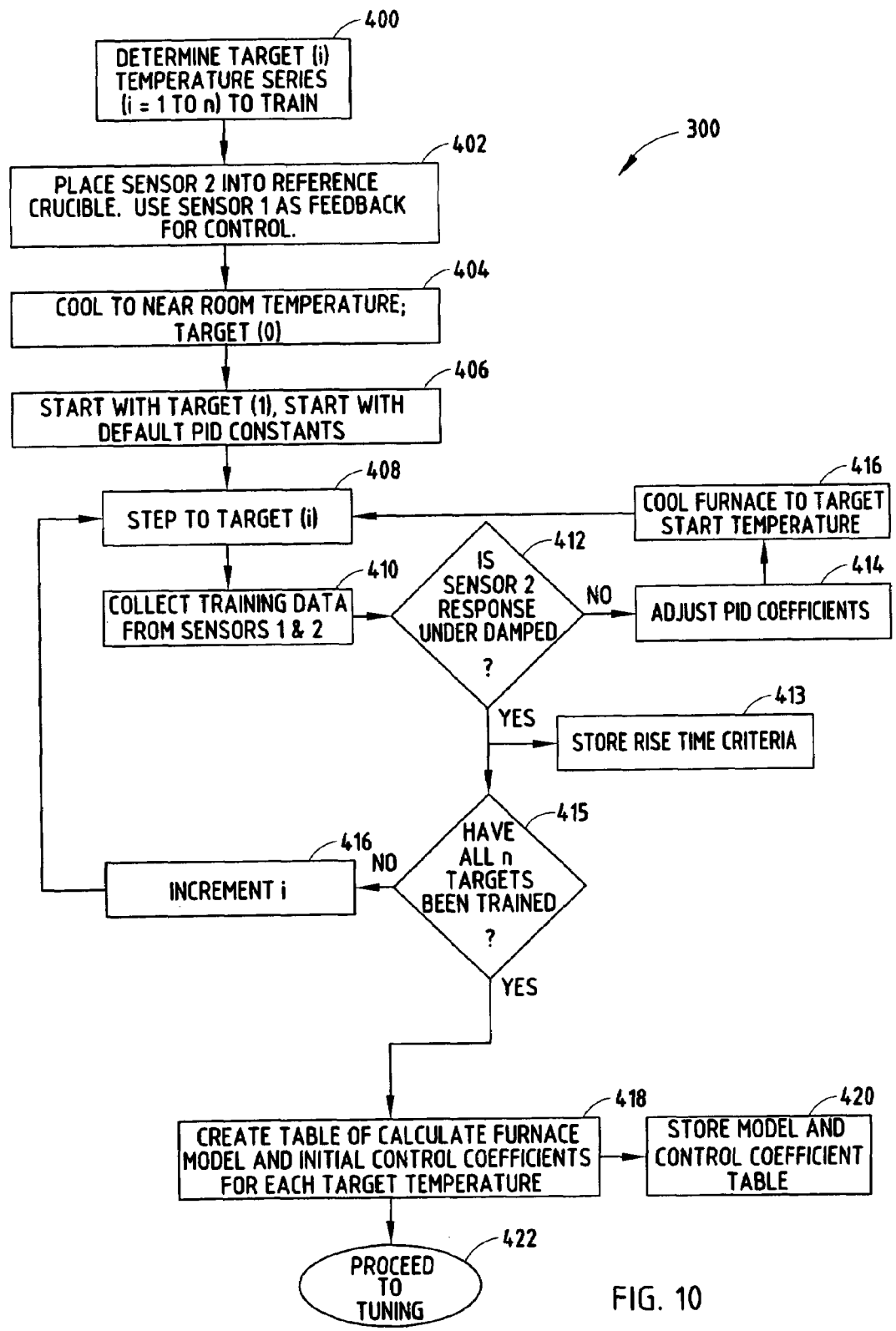
FIG. 10 is a flow diagram of the training portion of the algorithm for the temperature control.

The first step in the training mode shown in FIG. 10, as shown by step 400, is to determine a suitable series of target temperatures, start temperatures, target hold times, and required overshoot that will permit characterization of the crucible response over the entire operating range of the furnace from ambient to 1000° C. as shown in block 400. As an example, a series of start temperatures, target temperatures, and hold times are displayed in the following table.

TABLE 1

| Target | Start Temperature | Target Temperature | Hold Time |
|---|---|---|---|
| 1 | Ambient | 100° C. | 20 minutes |
| 2 | 100° C. | 200° C. | 20 minutes |
| 3 | 200° C. | 300° C. | 15 minutes |
| 4 | 300° C. | 400° C. | 15 minutes |
| 5 | 400° C. | 500° C. | 15 minutes |
| 6 | 500° C. | 600° C. | 15 minutes |
| 7 | 600° C. | 700° C. | 15 minutes |
| 8 | 700° C. | 800° C. | 10 minutes |
| 9 | 800° C. | 900° C. | 10 minutes |
| 10 | 900° C. | 1000° C. | 10 minutes |

The hold times, determined empirically, must be long enough for any oscillations to settle so that the steady state response can be observed and modeled. The training response is required to overshoot by 5 to 20° C. In addition, the model structure and sampling rate, and parameter estimation algorithm must be predefined so that the appropriate unknown model parameters can be determined. For the preferred embodiment, the sampling rate is 0.5 Hz, and the model has the following structure:

$$Y_{n-d} = a1 * Y_{n-d-1} + a2 * Y_{n-d-2} + b1 * U_n$$

Where:

$Y_{n-d}$: The crucible temperature predicted d sample periods in advance of the measurement of sensor 140

$Y_{n-d-1}$: The predicted crucible temperature one sample period previous $Y_{d-2}$: The predicted crucible temperature two sample periods previous $U_n$: The temperature measured by sensor 130.

d: The transport delay parameter a1, a2: Auto-regressive model parameters b1: Moving average model parameter Any of many regressive or block processing parameter estimation algorithms such as the method of Least Squares may be used to determine the parameters d, a1, a2, and b1. Parameter estimation routines typically iterate the value of the parameters in such a way as to minimize the summed square errors between the crucible response measured by sensor 140, and the estimated crucible response over the course of the observed response.

Next, the temperature sensor 140 is placed into the reference crucible, as shown by step 402, so that the actual crucible response can be measured. The furnace is allowed to cool to room temperature, as shown by step 404. The training begins with the first target temperature (i.e. 100° C.) 100° C., and a set of default PID constants determined empirically as indicated by step 406. The set point is stepped to the first target temperature, step 408, and data is collected from temperature sensors 130 and 140 for the predefined hold time period as indicated by step 410. It is necessary that the response of the crucible be slightly under damped such that the crucible temperature overshoots the target by at least a few degrees, and in the example, the overshoot is required to be 5 to 20° C. A slight temperature overshoot is required for the determination of an appropriate furnace rise time criteria to that target temperature and to assist in determining proper model parameters. If the response did not involve the appropriate degree overshoot as indicated by a 'no' decision in step 412, the PID coefficients are adjusted as shown by step 414. To make the response less damped, P can be increased, I increased, and/or D decreased. To make the response more damped, P can be decreased, I increased, and/or D increased. It is often appropriate to have a P only controller for training unless stability or response issues require a more complex controller. The furnace is then cooled to the start temperature for the target as shown by step 416, and the loop, including steps 408-412, is repeated.

Once sensor 140 determines that the crucible temperature has overshot the target temperature, resulting in a "yes" decision in step 412, at step 415 the system determines whether or not all ten steps (in the preferred embodiment) have been trained. If not, the program proceeds to increment to the next temperature target, as indicated by step 416, (i.e., from the initial cycle to 200° C.) and so forth until the 1000° C. level has been reached. During each of these intervals, the temperatures $T_1$ and $T_2$ for the internal furnace temperature and crucible temperature, respectively, are collected and stored, as indicated by step 410, and adjustments made to the PID coefficients to prevent over damping of the temperature detected by sensor 140. It is noted that the cooling process takes approximately an hour and the training step described so far can take several hours but, once accomplished, is stored and used for the future operation of the furnace.

Once all the targets have been trained, the algorithm proceeds to block 418 where the crucible model parameters, crucible delay, and initial PID control parameters for use in the tuning section are all calculated and stored as additional columns in Table 1 as shown by block 420. Because the response of sensor 130 to applied power is often non-linear, the initial PID control parameters are only estimates, and an iterative tuning process is often required to meet strict furnace performance criteria.

Figure 11A:
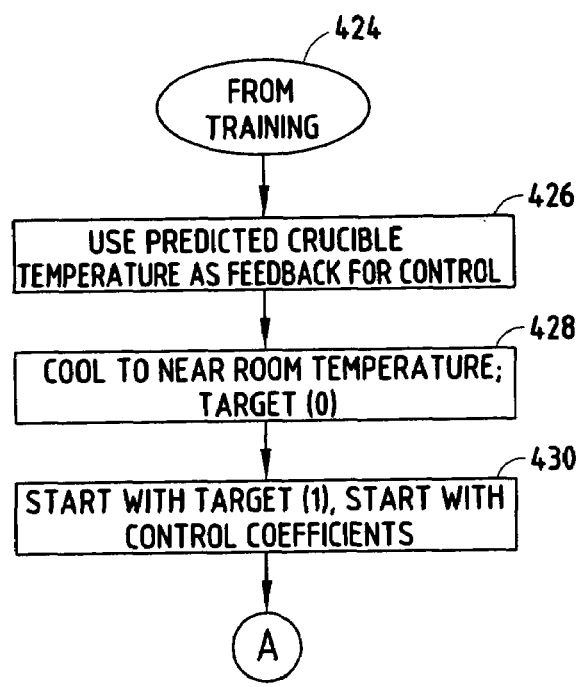
FIGS. 11A and 11B are the flow diagram for the program for the tuning of the predictive temperature control of the thermogravametric analyzer.
Figure 11B:
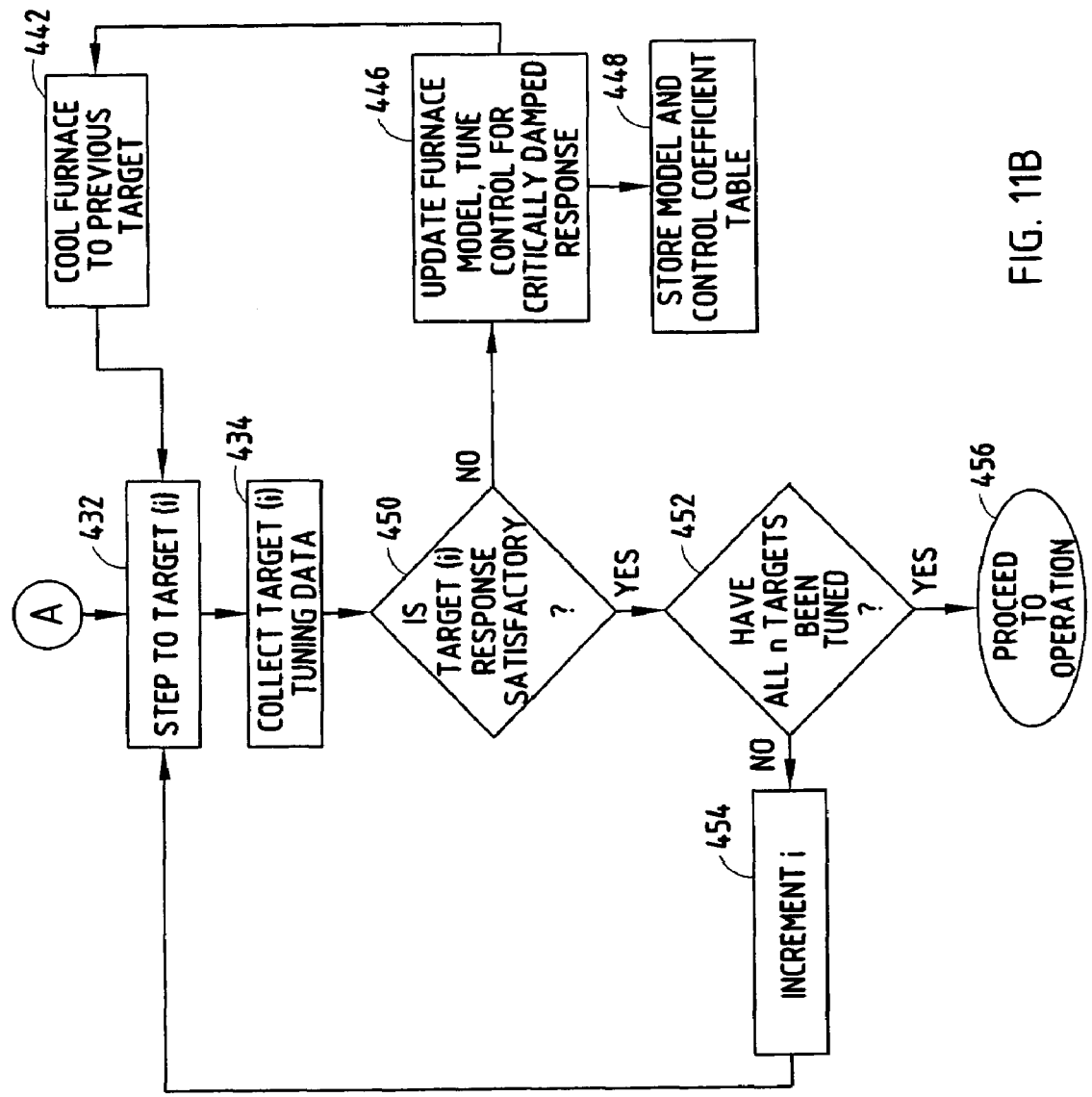

The program then proceeds from the training mode of FIG. 10 to the tuning mode shown in FIGS. 11A and 11B, as indicated by step 424. The tuning mode fine tunes the PID coefficients, as well as the crucible model and delay parameters, from the training mode to meet a set of performance criteria. For the preferred embodiment, the performance criteria includes rise time, error band, and control effort. The rise time is calculated for each target during the training phase. The error band is a temperature band around the target temperature within which the crucible response must stay for all time greater than or equal to the rise time criteria. The error band is ±2° C. for all targets. The control effort describes the appearance of the control signal output from the PID control block. It is desirable that the control signal be well-damped such that control signal oscillations settle quickly. An empirical condition may require consecutive damped oscillations to be one-third the amplitude of the proceeding oscillation.

In step 426, the signal $T_P$ is employed as a feedback signal for the temperature control and initially the furnace is cooled to room temperature, as seen by step 428. As indicated by step 430, the first target temperature (i.e., 100° C.) is introduced along with the PID coefficients calculated in step 418 of FIG. 10. The program then steps the furnace to the first temperature target (i.e., I=1 for 100° C.), as indicated by block 432, and energy is applied to the furnace heaters 104 while data from sensors 130 and 140 are collected, as indicated by step 434 until the target hold time has been reached. The performance of the furnace is compared to the performance criteria to determine if the furnace response is satisfactory as indicated in step 450. Satisfactory performance is defined as overshoot within the error band and maintaining the temperature within the error band from the criteria rise time until the end of the hold time. In addition, the control signal should be satisfactorily damped. If the target response is not satisfactory, indicated by a 'no' decision at step 450, the program proceeds to step 446 where the crucible model is updated and the control parameters are adjusted in an attempt to achieve a critically damped response. The new parameters are stored in the coefficient table shown by step 448. The furnace is again cooled to the target's start temperature indicated by step 442, and the tuning process is repeated until a satisfactory response is achieved as indicated by a 'yes' decision at step 450. At this point, the program advances to step 452 to test whether or not all of the target temperatures have been tuned. If the decision at step 452 is 'no', the next target is selected in step 454 and the tuning process is repeated for each of the target temperatures. Once all of the targets have been tuned as indicated by a 'yes' decision in step 452, the program proceeds to the operation mode as indicated by step 456 and shown in the diagram of FIG. 9B. In operation, sensor 140 is removed from the crucible and placed out of the way of the platter 18, so that crucibles containing samples can be admitted to the furnace and the furnace sequentially operated through any desired temperature profile for a sample while the crucibles are individually weighed throughout the duration of the programmed temperature profile.

In FIG. 9B at step 314, the operator enters for the type of sample being analyzed the ASTM or other temperature profile for a given sample. Thus, the data entry may include holding the sample at different temperatures for a variety of different times. By this time, the computer 202 has been programmed, however, to reach the target temperature as quickly and accurately as possible and this predictive temperature information is independent of the temperature profile data entered by the operator in step 314. The entered temperature profile is then applied to the summing junction, as indicated by step 316, where it is compared to the predicted crucible model temperature. The error signal is then applied to the predictive controller comprising the program computer 202 (FIGS. 7 and 8) and block 318, which applies pulse width modulated signals to the furnace heating elements 104. During the heating of the furnace, the predicted crucible temperature, as indicated by input 131, is used to determine by interpolation the appropriate predictive control parameters in block 318, the appropriate furnace model block 310, and the appropriate delay model block 312. The estimated crucible temperature predicted by the crucible model and delayed by the delay model is displayed to the operator, as indicated by block 320, for the duration of the entire temperature profile. The weight and temperature data, such as shown in FIG. 2, are collected by computer 202 during each temperature plateau and the computer provides, utilizing standard algorithms according to ASTM standards for different samples being analyzed, outputs to the printer 210 of the results of an analysis.

Thus, with the system of the present invention, a furnace control is provided which models the actual crucible temperature in response to measured furnace temperature so that a desired crucible temperature can be rapidly and accurately reached without temperature overshooting. By providing a separate temperature sensor positioned in the crucible, the dynamic temperature response of an individual furnace can be determined and the data stored and manipulated as described in connection with the above algorithm to provide an accurate and repeatable furnace temperature control system.

In the preferred embodiment of the invention, sample sizes range from 0.5 to 5 grams and ramp rates of approximately 15° C. per minute from ambient to 100° C. and 40° C. per minute from 100° C. to 1000° C. are achieved. Temperature accuracy was within plus or minus 2° C. at any given set point. Each individual furnace manufactured is trained as described above to determine the PID coefficients which may be unique to each furnace.

It will become apparent to those skilled in the art that various modifications to the preferred embodiment of the invention as described herein can be made without departing from the spirit or scope of the invention as defined by the appended claims.

The invention claimed is:

1. An analytical furnace comprising:
   a combustion furnace having a generally disk-shaped body with a cylindrical side wall;
   a resistive heating element positioned within said side wall and extending around said furnace;
   a crucible-holding platter positioned within said furnace and having a plurality of apertures therein;
   a plurality of crucibles positioned within said apertures of said platter, wherein said crucibles hold samples for combustion within said furnace;
   a control circuit for controlling the application of power to said heating element;
   a first temperature sensor positioned in fixed relationship within said furnace for detecting the furnace temperature at said fixed location;
   a second temperature sensor removably positionable within one of said crucibles positioned on said platter; and
   wherein said control circuit includes a temperature modeling cycle for correlating the temperature between said first and second temperature sensors during a cycle of furnace temperature steps and developing in response thereto optimum temperature control signals for increasing crucible temperatures to desired temperature levels.

2. The furnace as defined in claim 1 wherein said control circuit includes a processor which is programmed to measure temperatures from said first temperature sensor and said second temperature sensor and model the crucible temperature profile as a function of detected temperatures using a proportional, integral, and derivative (PID) process applied to temperature data obtained from said sensors.

3. The furnace as defined in claim 2 wherein said computer sequentially increases the temperature of the furnace through a plurality of temperature plateaus and determines PID data for each plateau.

4. The furnace as defined in claim 3 wherein said modeling data is further determined using an auto-regressive moving average approximation.

5. A thermogravametric analyzer comprising:
a combustion furnace having a generally disk-shaped body including a cylindrical side wall;
a resistive heater positioned within said side wall and extending around said furnace;
a crucible-holding platter positioned within said furnace and having a plurality of apertures therein;
a plurality of crucibles positioned within said apertures of said platter, wherein said crucibles hold samples for combustion within said furnace;
first and second temperature sensors; and
a control circuit for controlling the application of power to said heating element, wherein said control, circuit includes a processor which is programmed to measure the temperatures from said first temperature sensor which is positioned in fixed relationship within said furnace for detecting the furnace temperature at said fixed location and said second temperature sensor removably positionable within a crucible positioned on said platter, said control circuit modeling the crucible temperature profile as a function of detected furnace temperatures using a proportional, integral, and derivative (PID) process applied to temperature data obtained from said first and second temperature sensors.

6. The furnace as defined in claim 5 wherein said computer sequentially increases the temperature of the furnace through a plurality of temperature plateaus and determines PID data for each plateau.

7. The furnace as defined in claim 6 wherein modeling data is further determined using an auto-regressive moving average approximation.

8. A thermogravametric analyzer comprising:
a furnace having a cylindrical sidewall;
a balance with a weigh platform positioned within said furnace;
a plurality of crucibles for holding samples for analysis;
a rotatable support for holding said plurality of crucibles wherein said support is rotated to sequentially position crucibles on said weigh platform;
a heater within said cylindrical sidewall for heating said furnace;
a pair of temperature sensors including a first temperature sensor positioned in fixed relationship within said furnace and a second temperature sensor movable to be positioned within a crucible on said support; and
a control circuit coupled to said temperature sensors, said circuit including a processor programmed to obtain temperature data to model the crucible temperature as the furnace temperature is varied and to subsequently control the furnace temperature during operation.

9. The analyzer as defined in claim 8 wherein said processor is programmed to measure temperatures from said first temperature sensor and said second temperature sensor and model the crucible temperature profile as a function of detected temperatures using a proportional, integral, and derivative (PID) process applied to temperature data obtained from said sensors.

10. The analyzer as defined in claim 9 wherein said computer sequentially increases the temperature of the furnace through a plurality of temperature plateaus and determines PID data for each plateau.

11. The analyzer as defined in claim 10 wherein modeling data is further determined using an auto-regressive moving average approximation.

12. A thermogravametric analyzer comprising:
a disk-shaped furnace having a heating element;
a control circuit for controlling the application of power to said heating element;
a crucible-holding platter including a plurality of apertures for holding sample-holding crucibles;
a first temperature sensor positioned in fixed relationship within said furnace for detecting the furnace temperature at said fixed location;
a second temperature sensor removably positionable within a crucible positioned on said platter within said furnace; and
wherein said control circuit includes a temperature modeling cycle for correlating the temperature between said first and second temperature sensors during a cycle of step-wise increasing furnace temperature steps and developing in response thereto optimum temperature control signals for raising crucible temperatures to desired temperature levels while minimizing temperature overshoot.

13. The analyzer as defined in claim 12 wherein said control circuit includes a processor which is programmed to measure temperatures from said first temperature sensor and said second temperature sensor and model the crucible temperature profile as a function of detected temperatures using a proportional, integral, and derivative (PID) process applied to temperature data obtained from said sensors.

14. The analyzer as defined in claim 13 wherein said computer sequentially increases the temperature of the furnace through a plurality of temperature plateaus and determines PID data for each plateau.

15. The analyzer as defined in claim 14 wherein modeling data is further determined using an auto-regressive moving average approximation.

\* \* \* \* \*